United States Patent [19]
Confalone et al.

[11] 3,979,396
[45] Sept. 7, 1976

[54] SYNTHESIS OF BIOTIN

[75] Inventors: Pasquale Nicholas Confalone, Bloomfield; Milan Radoje Uskokovic, Upper Montclair; Giacomo Pizzolato, Belleville, all of N.J.

[73] Assignee: Hoffmann-La Roche Inc., Nutley, N.J.

[22] Filed: Dec. 3, 1973

[21] Appl. No.: 420,811

[52] U.S. Cl............................ 260/293.68; 424/244; 424/267; 424/274; 424/275; 260/239 BF; 260/326.35; 260/332.2 A
[51] Int. Cl.[2]........................................ C07D 405/00
[58] Field of Search................ 260/293.51, 332.2 A, 260/293.68

[56] References Cited
FOREIGN PATENTS OR APPLICATIONS
467,900    9/1950    Canada............................ 260/332.2

OTHER PUBLICATIONS

Harris et al., "J.A.C.S.", (1944), vol. 66, pp. 1756, 1757.

Groggins, "Processes In Organic Synthesis", fourth ed., (1952), p. 489.

*Primary Examiner*—James O. Thomas, Jr.
*Assistant Examiner*—A. Siegel
*Attorney, Agent, or Firm*—Samuel L. Welt; Bernard S. Leon; Richard A. Gaither

[57] ABSTRACT

Synthesis of biotin from 4-carbomethoxy-2-(4,5-dihydrothiophen-3(2H)-one)-valeric acid methyl ester, and dihydrothiophene intermediates in this synthesis.

7 Claims, No Drawings

SYNTHESIS OF BIOTIN

SUMMARY OF THE INVENTION

This invention is directed to a process for selectively synthesizing d, l-biotin, which has the structural formula:

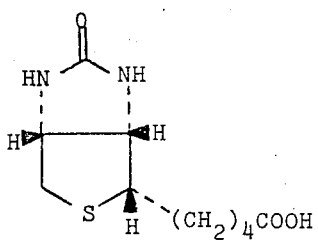

from a 4,5-dihydrothiophene compound of the formula:

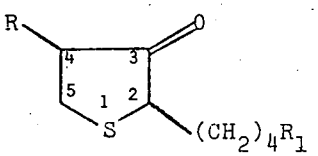

wherein R is carboxy protected with a group convertible thereto by hydrolysis; and $R_1$ is carboxy or carboxy protected with a group convertible thereto by hydrolysis.

By means of this process, biotin can be economically produced in high yields from the 4,5-dihydrothiophene of formula I.

DETAILED DESCRIPTION OF THE INVENTION

As used throughout this application, the term "carboxy protected with a group convertible thereto by hydrolysis" comprehends any conventional organic acid protecting group which can be removed by hydrolysis. The preferred organic acid protecting groups are the esters. Any conventional ester that can be hydrolyzed to yield the acid can be utilized as the protecting group. Exemplary esters useful for this purpose are the lower alkyl esters, particularly methyl and ethyl esters, the aryl esters, particularly phenyl ester, and the aryl lower alkyl esters, particularly benzyl ester.

As also used throughout this application, the term "hydrocarbyl" denotes a monovalent substituent consisting solely of carbon and hydrogen. The term "aliphatic" with reference to hydrocarbyl denotes straight chain and brancheed chain groups of 1 to 20 carbon atoms which are saturated or which include one or more olefinic and/or acetylenic carbon to carbon bonds, but which include no aromatic unsaturation, such as methyl, ethyl, allyl, propargyl, hexenyl and decyl. The term "cycloaliphatic" with reference to hydrocarbyl denotes mononuclear groups of 3 to 7 carbon atoms and polynuclear groups of 7 to 17 carbon atoms, which are saturated or which contain olefinic and/or acetylenic carbon to carbon bonds but which contain no aromatic unsaturation and which can contain one or more aliphatic hydrocarbyl moieties, such as menthyl, bornyl and cholesteryl.

As further used throughout this application, the term "lower alkyl" denotes straight chain and branched chain saturated aliphatic hydrocarbyl groups having from 1 to 8 carbon atoms, such as methyl, ethyl and propyl, preferably methyl. As also used herein, the term "aryl" signifies mononuclear aromatic hydrocarbyl groups of 6 to 13 carbon atoms, such as phenyl and tolyl, which can be unsubstituted or substituted in one or more positions with a lower alkylenedioxy, a halogen, a nitro, a lower alkyl or a lower alkoxy substituent, and polynuclear aryl groups of 10 to 17 carbon atoms, such as naphthyl, anthryl, phenanthryl and azulyl, which can be substituted with one or more of the aforementioned groups. The preferred aryl groups are the substituted and unsubstituted mononuclear aryl groups, particularly phenyl. As further used herein, the term "aryl lower alkyl" comprehends groups wherein aryl and lower alkyl are as defined above, particularly benzyl. As still further used herein, the term "lower alkoxy" comprehends groups having from 1 to 7 carbon atoms such as methoxy and ethoxy. Also herein, the term "halogen" or "halo", unless otherwise stated, comprehends fluorine, chlorine, bromine and iodine. Further herein, the term "lower alkylenedioxy" comprehends lower alkylenedioxy groups having 1 to 4 carbon atoms, such as methylenedioxy and ethylenedioxy.

As still further used throughout this application, in the pictorial representations of the compounds of this application, a thickened tapered line (◂) indicates a substituent which is in the β-orientation (above the plane of the molecule), a dotted line (-----) indicates a substituent which is in the β/orientation (below the plane of the molecule) and a wavy line (~) indicates a substituent which is in either the α- or β-orientation. It is to be understood that the pictorial representations of the compounds given througout the specification are set forth for convenience and are to be construed as inclusive of other forms, including enantiomers and racemates, and are not to be construed as limited to the particular form shown.

In accordance with this invention, d,l-biotin is obtained by first converting the 4,5-dihydrothiophene of formula I to an amino-dihydrothiophene of the formula:

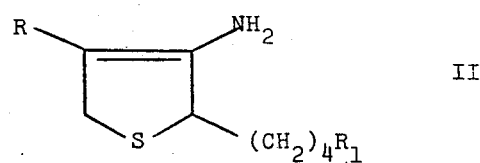

wherein R and $R_1$ are as above.

In carrying out this reaction, the 4,5-dihydrothiophene of formula I is treated with an ammonium salt. In this reaction, any conventional ammonium salt can be utilized, such as the ammonium lower alkanoates, ammonium benzoates and ammonium halides. The preferred ammonium slats are ammonium formate, ammonium acetate and ammonium chloride, particularly ammonium formate. This reaction is suitably carried out in a conventional, inert organic solvent. The preferred inert organic solvents are the lower alkanols, particularly methanol and ethanol. In carrying out this reaction, temperature and pressure are not critical, and temperatures of about 50°C. to 110°C. and atmospheric pressure are suitably utilized. Preferably, temperatures of about 70°C. are utilized in this reaction.

In carrying out the conversion of the 4,5-dihydrothiophene of formula I to the amino-dihydrothiophene of formula II, it is preferred that $R_1$ be carboxy protected with a group convertible thereto by hydrolysis, especially a lower alkyl ester group, particularly a methyl ester group. In accordance with this preferred aspect of the process of this application, the amino-dihydrothiophene of formula II, wherein $R_1$ is carboxy protected with a group convertible thereto by hydrolysis, is then converted to an amino acid of the formula:

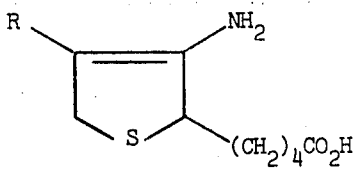   III wherein R is as above.

This reaction is carried out by the basic hydrolysis of the amino-dihydrothiophene of formula II. In caarrying out this reaction, it has been surprisingly found that any conventional procedure for basic hydrolysis can be suitably utilized to selectively hydrolyze the 2-valerate group [i.e., $-(CH_2)_4R_1$] of the amino-dihydrothiophene of formula II to form the amino acid of formula III in high yields. This hydrolysis can be carried out in any conventional inert solvent. The preferred solvents are the lower alkanols, particularly methanol and ethanol, and the aqueous ether solvents, preferably the aqueous dilower alkyl ethers, particularly diethyl ether, and the aqueous cyclic ethers, particularly tetrahydrofuran and dioxane. In this reaction, any conventional base can be utilized. Among the preferred bases are the alkali metal hydroxides, such as sodium, potassium and lithium hydroxide, and the alkaline earth metal hydroxides, such as calcium and magnesium hydroxide, especially the alkali metal hydroxides. In this hydrolysis, temperature and pressure are not critical, and this reaction can be suitably carried out at from 0°C. to about 100°C. and at atmospheric pressure. Preferably, this reaction is carried out at reflux, especially at about 70°C.

The amino acid of formula III is then converted to a mixed anhydride of the formula:

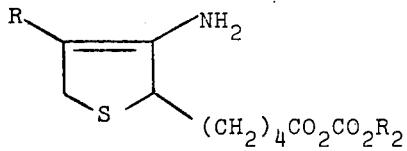   IV wherein R is as above; and $R_2$ is lower alkyl or phenyl; which is in turn converted to an amide of the formula:

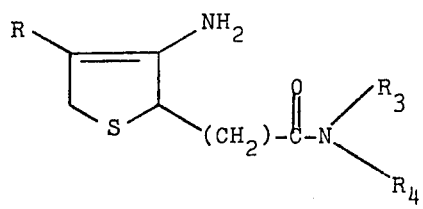   V wherein R is as above; $R_3$ is individually hydrogen, lower alkyl, aryl, or aryl lower alkyl; and $R_4$ is individually lower alkyl, aryl or aryl lower alkyl; or $R_3$ and $R_4$ taken together with the nitrogen atom form a saturated or unsaturated, heterocyclic moiety of 4 to 6 carbon atoms.

The compound of formula IV can be obtained by treating the amino acid of formula III with a lower alkyl or phenyl chloroformate, preferably a lower alkyl chloroformate. This reaction can be suitably carried out in an inert organic solvent in the presence of a base. In this reaction, any conventional inert organic solvent can be utilized. The preferred inert organic solvents are the ethers, such as the dilower alkyl ethers, tetrahydrofuran and dioxane, and the aqueous lower alkanols, such as methanol and ethanol. In this reaction, any conventional base can be utilized. Among the bases which can be utilized are the primary, secondary and tertiary amines, including the monolower alkyl, dilower alkyl and trilower alkyl amines, such as triethylamine, dimethylamine and isopropylamine, and the cyclic amines, such as pyridine; the alkali metal hydroxides, such as sodium hydroxide; and the alkaline earth metal hydroxides, such as calcium hydroxide. The preferred bases in this reaction are the amines. In carrying out this reaction, temperature and pressure are not critical, and this reaction can be suitably carried out at from about $-10°C$. to about 40°C. and at atmospheric pressure. Preferably, this reaction is carried out at about 25°C.

The resulting anhydride of formula IV can then be treated, preferably in the solution in which it was formed, with an amine to form the corresponding amide of formula V. In this reaction, any conventional primary or secondary amine can be utilized. The preferred amines are the lower alkyl, aryl, aryl lower alkyl and saturated and unsaturated cyclic amines of 4 to 6 carbon atoms, such as methylamine, diethylamine, aniline, pyridine, piperidine and benzylamine. This reaction is suitably carried out in an inert organic solvent. In this reaction any conventional inert organic solvent can be utilized, such as the ethers and aqueous alkanols used in converting the amino acid of formula III to the anhydride of formula IV. In carrying out this reaction, temperature and pressure are not critical, and the reaction can be suitably carried out at from about $-10°C$. to about 40°C. and atmospheric pressure. Preferably, this reaction is carried out at about 25°C.

The amide of formula V is then converted to a bisamido compound of the formula:

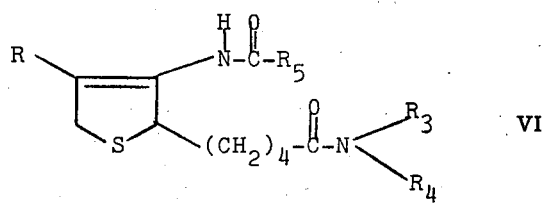   VI wherein R, $R_3$ and $R_4$ are as above; and $R_5$ is lower alkyl, aryl, or aryl lower alkyl.

This reaction can be suitably carried out by treating the amide of formula V with a lower alkanoic acid anhydride, such as acetic anhydride, or an aryl lower alkanoic acid anhydride, such as benzoic acid anhydride, preferably a lower alkanoic acid anhydride. This reaction is preferably carried out in the presence of a strong acid. In this reaction, any conventional strong acid can be utilized. Among the strong acids which can be utilized are the mineral acids, such as sulfuric acid, hydrochloric acid, perchloric acid, and phosphoric acid, and the strong organic acids, such as trifluoroacetic acid, methane sulfonic acid, and p-toluene sulfonic acid. This reaction can be carried out in an inert organic solvent. In this reaction, any conventional inert organic solvent can be utilized, such as the ether solvents, particularly the dilower alkyl ethers, tetrahydrofuran and dioxane, and the aromatic solvents, such as benzene and toluene. Preferably, this reaction is carried out in an excess of the acid anhydride, which serves as the solvent medium. In carrying out this reaction, temperature and pressure are not critical, and the reaction can be suitably carried out at from −20°C. to +50°C. and at atmospheric pressure. Preferably, this reaction is carried out at about room temperature (about 22° C.).

The bis-amido compound of formula VI is then converted to a bisamido acid compound of the formula:

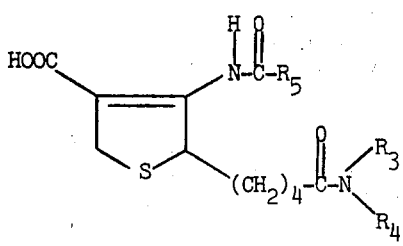

VII wherein $R_3$, $R_4$ and $R_5$ are as above.

This reaction can be suitably carried out by subjecting the bis-amido compound of formula VI to a conventional, basic hydrolysis. In carrying out this reaction, the conditions utilized above for hydrolyzing the amino-dihydrothiophene of formula II can be utilized. This reaction is preferably carried out at about room temperature.

The bis-amido acid of formula VII is then converted to a 4-carb(alkoxy or phenoxy)carbonyl compound of the formula:

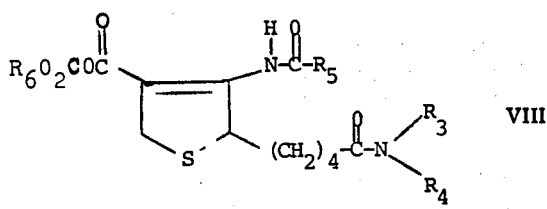

VIII wherein $R_3$, $R_4$ and $R_5$ are as above; and $R_6$ is lower alkyl or phenyl;
which is in turn converted to a 3-[N-carb(alkoxy or phenyloxy)acylamido] compound of the formula:

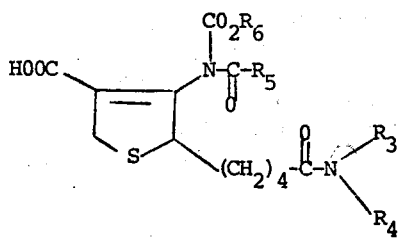

IX wherein $R_3$, $R_4$, $R_5$ and $R_6$ are as above;

which is in turn converted to a 3-[N-carb(alkoxy or phenoxy)acylamido] -4-carb(alkoxy or phenoxy)carbonyl compound of the formula:

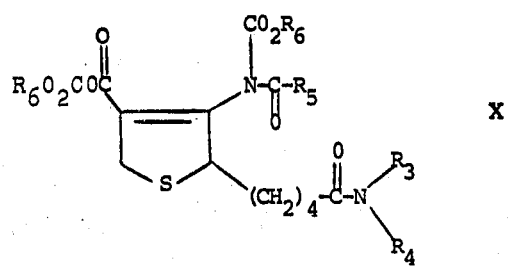

X wherein $R_3$, $R_4$, $R_5$ and $R_6$ are as above;
and which is in turn converted to an azidocarbonyl compound of the formula:

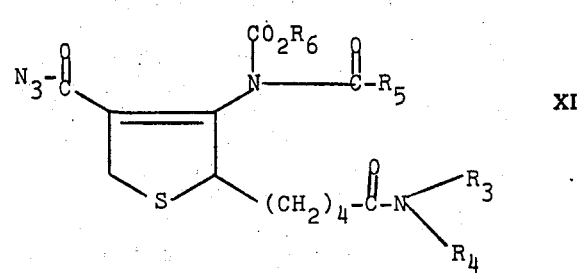

XI wherein $R_3$, $R_4$, $R_5$ and $R_6$ are as above.

The 4-carb(alkoxy or phenoxy)carbonyl compound of formula VIII can be obtained and in turn converted to the 3-[N-carb(alkoxy or phenoxy)acylamido] compound of formula IX, which can be in turn converted to the 3-[N-carb(alkoxy or phenoxy)acylamino]-4-carb-(alkoxy or phenoxy)carbonyl compound of formula X, by treating the bis-amido acid of formula VII with a lower alkyl or phenyl chloroformate in the presence of a base. This reaction can be carried out in a conventional manner, such as by utilizing the procedure, set forth above, for converting the amino acid of formula III to the mixed anhydride of formula IV.

The azidocarbonyl compound of formula XI can then be obtained by treating the compound of formula X in a conventional manner with an alkali metal azide or an alkaline earth metal azide. This reaction can be carried out in a conventional, inert organic solvent. Preferably, this reaction is carried out in the reaction mixture in which the compound of formula X was formed. In carrying out this reaction, temperature and pressure are not critical, and this reaction can be suitably carried out at from about −10°C. to about 30°C. and at atmospheric pressure. Preferably, this reaction is carried out at about 0°C.

The azidocarbonyl compound of formula XI is then converted to an isocyanate compound of the formula:

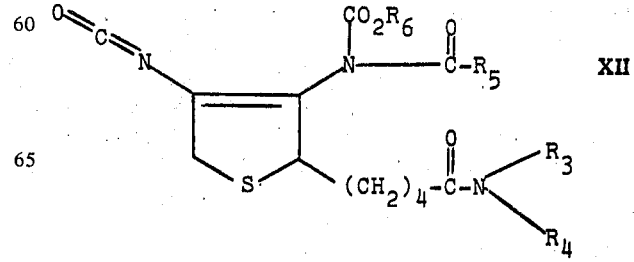

XII wherein $R_3$, $R_4$, $R_5$ and $R_6$ are as above; which is in turn converted to a urethane compound of the formula:

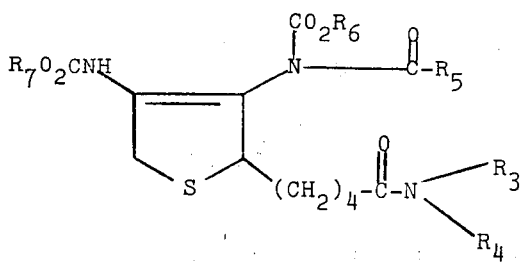

XIII wherein $R_3$, $R_4$, $R_5$ and $R_6$ are as above; and $R_7$ is aliphatic hydrocarbyl, cycloaliphatic hydrocarbyl or aryl lower alkyl.

The isocyanate compound of formula XII can be obtained and in turn converted to the urethane compound of formula XIII by heating the azidocarbonyl compound of formula XI in the presence of an alcohol. In this reaction, any conventional alcohol can be utilized. The preferred alcohols are the aliphatic hydrocarbyl alcohols, the cycloaliphatic hydrocarbyl alcohols, and the aryl lower alkyl alcohols, such as methanol, ethanol, allyl alcohol, propargyl alcohol, borneol, menthol, benzyl alcohol and cholesterol. Especially preferred alcohols for use in this process are the lower alkanols and the phenyl lower alkanols. This process can be suitably carried out in the presence of an inert organic solvent. In this process, any conventional inert organic solvent can be utilized, as for example chloroform, benzene and hexane. Preferably, this reaction is carried out in an excess of the alcohol, which serves as the solvent medium. In carrying out this reaction, temperature and pressure are not critical, and temperatures of from about 50°C. to about 110°C. and atmospheric pressure can be suitably utilized. Preferably, this reaction is carried out at about 70°C to 75°C.

The urethane compound of formula XIII is then converted to a bis-urethane compound of the formula:

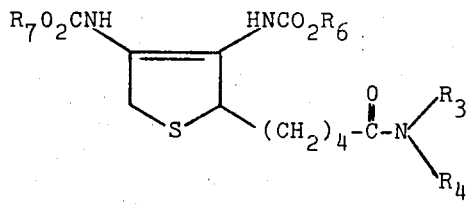

XIV wherein $R_3$, $R_4$, $R_6$ and $R_7$ are as above.

The bis-urethane compound of formula XIV can be obtained by the basic hydrolysis of the urethane compound of formula XIII. It has been surprisingly found that the principal result of this basic hydrolysis is to selectively remove the $-\overset{O}{\underset{\parallel}{C}}-R_5$ group from the urethane molecule. This reaction can be carried out in a conventional manner, such as by utilizing the procedure set forth above for the basic hydrolysis of the amino-dihydrothiophene of formula II. The reaction is preferably carried out at about room temperature (about 22°C.).

The bis-urethane compound of formula XIV is then converted to a tetrahydrothiophene compound of the formula:

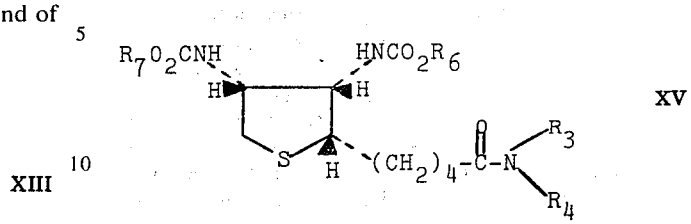

XV wherein $R_3$, $R_4$, $R_6$ and $R_7$ are as above.

The tetrahydrothiophene compound of formula XV can be obtained by the catalytic hydrogenation of the bis-urethane compound of formula XIV in the presence of an acid. In carrying out this reaction, any conventional noble metal hydrogenation catalyst, such as palladium, platinum, ruthenium or rhodium, can be utilized. This reaction is suitably carried out in an inert organic solvent in which the bis-urethane compound of formula XIV can catalytic quantities of the acid are soluble. Among the preferred, inert organic solvents are the lower alkanols, such as methanol and ethanol, and the cyclic ethers, such as dioxane and tetrahydrofuran. Especially preferred solvents for carrying out this reaction are the lower alkanoic acids, particularly glacial acetic acid, in which the addition of catalytic quantities of an acid to the solvent may be dispensed with. In carrying out this reaction in an inert solvent other than an alkanoic acid, any conventional carboxylic acid may be used to catalyze the hydrogenation. The preferred acids for this purpose are the lower alkanoic acids, such as formic, acetic and pentanoic acid, the lower alkane dicarboxylic acids, such as succinic acid, and the aryl lower alkanoic acids, such as benzoic acid. In carrying out this reaction, particular temperatures and pressures are not critical, and the reaction can be suitably carried out at from about 50°C. to about 110°C. and at pressures of from about 1000 to about 3000 psi. Preferably, this reaction is carried out at about 75°C.

The tetrahydrothiophene compound of formula XV is then converted to d,1-biotin. D,1-biotin can be obtained by hydrolyzing the tetrahydrothiophene compound of formula XV with a strong base. This reaction can be carried out in a conventional manner, utilizing any conventional strong base, such as the alkali metal hydroxides and alkaline earth metal hydroxides. In this reaction, the alkali metal hydroxides, such as sodium, potassium and lithium hydroxide, are preferred. This reaction can be suitably carried out in water or in an aqueous inert organic solvent. In this reaction, any conventional inert organic solvent can be utilized, such as the lower alkanols, particularly methanol and ethanol, and the ether solvents, such as diethyl ether, tetrahydrofuran and dioxane. Preferably, this reaction is carried out in water. In carrying out this reaction, temperature and pressure are not critical, and the reaction can be suitably carried out at temperatures of 50°C. to about 110°C. and at atmospheric pressure. Preferably, this reaction is carried out at about 75°C.

Formed as a by-product of the hydrolysis of the tetrahydrothiophene compound of formula XV, whereby d,1-biotin is formed, is a bis-amino compound of the formula:

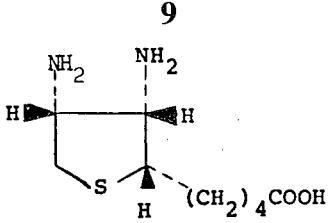

XVI

D,1-biotin can be obtained from the bis-amino compound of formula XVI in a conventional manner, such as by treating the bis-amino compound with phosgene in the presence of an aqueous base. In carrying out this reaction, any conventional aqueous base can be utilized. The preferred bases are the alkali metal carbonates. In carrying out this reaction, temperature and pressure are not critical, and the reaction can be suitably carried out at from −20°C. to +75°C. and at atmospheric pressure. Preferably this reaction is carried out at about 0°C.

D,1-biotin can also be obtained from the urethane compound of formula XIII by first catalytically hydrogenating the urethane compound of formula XIII to form a urethane-tetrahydrothiophene compound of the formula:

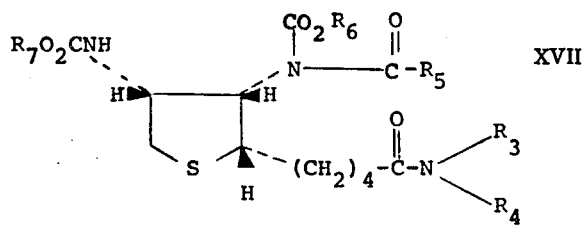

XVII wherein $R_3$, $R_4$, $R_5$, $R_6$ and $R_7$ are as above.

This hydrogenation can be suitably carried out according to the procedure set forth above for hydrogenating the bis-urethane compound of formula XIV to form the tetrahydrothiophene of formula XV.

The urethane-tetrahydrothiophene of formula XVII is then hydrolyzed with a strong base to form the bis-amino compound of formula XVI. This reaction can also be carried out in a conventional manner, such as by utilizing the procedure, set forth above, for converting the tetrahydrothiophene compound of formula XV to d,1-biotin.

The bis-amino compound of formula XVI can be conveniently converted to d,1-biotin in the manner set forth above.

The biotin which is obtained by the process of this application can be obtained in pure form as the free acid, or, if desired, can be esterified in a conventional manner with a lower alkanol to form the corresponding ester.

The 4,5-dihydrothiophene compounds of formula I, which are the starting materials for the process described in this application, are generally known. In Baker et al, J. Org. Chem., 12, 167 (1947), the preparation of 4-carbomethoxy-2-(4,5-dihydrothiophen-3(2H)-one)valeric acid methyl ester is described. Utilizing conventional hydrolysis and trans-esterification procedures, this dihydrothiophene compound can be conveniently converted to form the other 4,5-dihydrothiophene compounds of formula I of this application.

The examples which follow further illustrate this invention. All temperatures are in degrees Centigrade.

EXAMPLE 1

A solution of 60.0 g (.182 mole) 4-carbomethoxy-2-(4,5-dihydrothiophen-3(2H)-one)valeric acid methyl ester in 550 ml. absolute ethanol was treated with 91.6 g (1.45 moles) of ammonium formate. The reaction was brought up to reflux and maintained at that temperature for 5.0 hrs. The reaction mixture was cooled, concentrated, and partitioned in a separatory funnel between 200 ml dichloromethane and 150 ml water. The aqueous phase was extracted further three times with 50 ml portions of dichloromethane. The organic extracts were pooled, dried over anhydrous sodium sulfate, and evaporated. 50.0 g (.182 mole, 100%) 3-amino-4-carbomethoxy-2,5-dihydro-2-thiophenevaleric acid methyl ester was obtained as a colorless oil.

EXAMPLE 2

To a solution of 27.3 g (.1 mole) of 3-amino-4-carbomethoxy-2,5-dihydro-2-thiophenevaleric acid methyl ester in 250 ml dry methanol was added 4.0 g (0.1 mole) of sodium hydroxide pellets. The reaction mixture was refluxed 4.0 hrs, cooled and concentrated to a volume of 50 ml. The residue was taken up in 80 ml dichloromethane and transfered to a separatory funnel. After the addition of 150 ml of 10% by weight aqueous sodium bicarbonate solution, the aqueous layer was extracted twice with 50 ml portions of dichloromethane. The organic phases were combined, dried over anhydrous sodium sulfate, and evaporated to yield 6.4 g (0.0234 mole) of recovered starting material. The aqueous phase was adjusted to pH 1 with 6 N hydrochloric acid and extracted three times with 75 ml portions of dichloromethane. The organic phases were pooled, dried over anhydrous sodium sulfate, and evaporated to yield 18.3 g (0.071 mole, 71%) of 3-amino-4-carbomethoxy-2,5-dihydro-2-thiophenevaleric acid as a tan solid, upon trituration with pet. ether.

The recovered starting material, 6.4 g (0.0234 mole) was dissolved in 70 ml dry methanol and treated with 1.0 g (0.025 mole) sodium hydroxide. The mixture was refluxed 5.0 hrs, cooled concentrated, and taken up in 80 ml dichloromethane. The organic phase was treated in a separatory funnel with 100 ml of 10% by weight aqueous sodium bicarbonate solution. The aqueous phase was extracted twice with 40 ml portions of dichloromethane. The aqueous phase was acidified to pH 1 with 6 N hydrochloric acid and extracted two times with 50 ml portions of dichloromethane. The organic phases were cooled, dried over anhydrous sodium sulfate, and evaporated to dryness to afford an additional 5.3 g (0.021 mole, 21%) of 3-amino-4-carbomethoxy-2,5-dihydro-2-thiophenevaleric acid; m.p. 98°–102°C.

EXAMPLE 3

To a solution of 5.18 g (0.020 mole) of 3-amino-4-carbomethoxy-2,5-dihydro-2-thiophenevaleric acid in 60 ml tetrahydrofuran was added 2.8 ml (.020 mole) of triethylamine in one portion at 25°C. At this point, 1.98 ml (0.020 mole) of ethyl chloroformate was added over a one minute period. After stirring for 1.5 hrs at 25°, the 3-amino-4-carbomethoxy-2,5-dihydro-2-thiophenevaleric acid anhydride with monoethyl carbonic acid was produced in the reaction mixture. Then, 2.0 ml (0.020 mole) of piperidine was added to the mixture, and the reaction was allowed to proceed at 25°C. for 2 hrs. At this point, the reaction mixture was concentrated and taken up in 100 ml of dichloromethane, washed with 50 ml of 10% by weight aqueous sodium bicarbonate solution, followed by treatment with 50 ml of 1N hydrochloric acid. The resulting organic phase was dried over anhydrous sodium sulfate and evaporated to afford 6.5 g (.02 mole, 100%) of pure 3-amino-4-carbomethoxy-2,5-dihydro-2-thiophenevaleric acid piperidide as a pale yellow oil.

EXAMPLE 4

To a solution of 7.4 g (.0226 mole) of 3-amino-4-carbomethoxy-2,5-dihydro-2-thiophenevaleric acid piperidide in 50 ml of acetic anhydride was added dropwise 1 ml of perchloric acid. The reaction was stirred for 1.5 hrs. and then was worked up. Acetic anhydride was removed under vacuum. The residue was partitioned between 50 ml of 10% by weight aqueous sodium bicarbonate solution and 150 ml of methylene chloride. The basic, aqueous phase was extracted three times with 30 ml portions of methylene chloride. The methylene chloride phase was dried over sodium sulfate, filtered, and evaporated to yield 8.2 g (0.022 mole, 100%) of 3-acetamido-4-carbomethoxy-2,5-dihydro-2-thiophenevaleric acid piperidide.

EXAMPLE 5

To a solution of 8.2 g (.022 mole) of 3-acetamido-4-carbomethoxy-2,5-dihydro-2-thiophenevaleric acid piperidide in 80 ml of methanol was added 40 ml of 1 N sodium hydroxide. The reaction was stirred at room temperature (22°C.) for 3 hrs. and was immediately worked up by first removing methanol under vacuum. The aqueous, basic residue was partitioned between 50 ml of water and 100 ml of methylene chloride. The basic, aqueous phase was extracted three times with 30 ml portions of methylene chloride. The methylene chloride was dried over sodium sulfate, filtered, and evaporated to afford 2.45 g (0.0075 mole, 34%) of 3-amino-4-carbomethoxy-2,5-dihydro-2-thiophenevaleric acid piperidide.

The aqueous basic phase was acidified with 50 ml of 1 N hydrochloric acid and extracted three times with 75 ml of methylene chloride. The organic phase was dried over sodium sulfate, filtered, and evaporated to afford 4.8 g [0.0136 moles, 61% (94% corrected)] of 3-acetamido-4-carboxy-2,5-dihydro-2-thiophenevaleric acid piperidide.

EXAMPLE 6

2.12 g (0.0060 moles) of 3-acetamido-4-carboxy-2,5-dihydro-2-thiophenevaleric acid piperidide was dissolved in 25 ml acetone to which 1.3 ml water had been added, and the solution was cooled in an ice bath for 15 min. At this point 1.8 ml (.0063 mole) of triethylamine was added in 25 ml acetone, followed immediately by the dropwise addition of 1.23 ml. (0.0063 mole) of ethyl chloroformate in 2.7 ml of acetone over a 10 minute period. The reaction was stirred at 0°C. for one hour to form 3-acetamido-4-carbethoxycarbonyl-2,5-dihydro-2-thiophenevaleric acid piperidide, which was converted to 3-(N-carbethoxyacetamido)-4-carboxy-2,5-dihydro-2-thiophenevaleric acid piperidide, and which was converted to 3-(N-carbethoxyacetamido)-4-carbethoxycarbonyl-2,5-dihydro-2-thiophenevaleric acid piperidide. A solution of 0.8 g. (0.0063 mole) sodium azide in 5 ml. water was added dropwise over a period of 5 minutes. The reaction was further stirred at 0°C. for 2 hrs. The reaction mixture was then partitioned between 100 ml. of dichloromethane and 75 ml. of ice water. The aqueous phase was extracted three times with anhydrous sodium sulfate to yield 2.8 g. (0.0060 mole, 100%) of 4-azidocarbonyl-3-(N-carbethoxyacetamido)-2,5-dihydro-2-thiophenevaleric acid piperidide as a colorless oil.

EXAMPLE 7

2.8 g (.006 moles) of 4-azidocarbonyl-3-(N-carbethoxyacetamido)-2,5-dihydro-2-thiophenevaleric acid piperidide was dissolved in 50 ml. of methanol and brought slowly up to reflux over a 15 minute period. The reaction was allowed to proceed for 5 hrs. at this temperature. Formed as an intermediate in the reaction mixture was 3-(N-carbethoxyacetamido)-4-isocyanato-2,5-dihydro-2-thiophenevaleric acid piperidide. The methanol was then removed, and 2.33 g. (0.0056 mole, 85%) of 3-(N-carbethoxyacetamido)-4-carbomethoxyamino-2,5-dihydro-2-thiophenevaleric acid piperidide was obtained as a colorless oil.

EXAMPLE 8

0.1 g (.000219 moles) of 3-(N-carbethoxyacetamido)-4-carbomethoxyamino-2,5-dihydro-2-thiophenevaleric acid piperidide was dissolved in 10 ml of tetrahydrofuran, and to this solution, 2 ml of 1 N sodium hydroxide was added. The heterogeneous solution was stirred for 2 hrs. and was then worked up immediately. Tetrahydrofuran was removed under vacuum, and the aqueous basic residue was partitioned between 30 ml of water and 20 ml of dichloromethane. The aqueous phase was extracted three times with 20 ml portions of dichloromethane. The organic phases were combined, dried over anhydrous sodium sulfate, filtered, and evaporated, giving 0.08 g (0.000196 moles, 90%) of 3-carbethoxyamino-4-carbomethoxyamino-2,5-dihydro-2-thiophenevaleric acid piperidide. Upon trituration with pet. ether, the product was obtained as a solid which could be recrystallized from ethyl acetate to give white crystals; m.p. 120°–122°.

EXAMPLE 9

0.347 g (0.0008402 moles) of 3-carbethoxyamino-4-carbomethoxyamino-2,5-dihydro-2-thiophenevaleric acid piperidide was dissolved in 200 ml of glacial acetic acid and subjected to 1800 psi hydrogen gas in a steel autoclave at 50°C. for 10 hrs. in the presence of 2 g of 10% Pd/C catalyst. After cooling to room temperature (22°C.), the autoclave was vented, the catalyst filtered, and washed with 100 ml of glacial acetic acid. The solvent was removed under high vacuum to afford 0.320 g (0.00077 mole, 91%) of all cis d, 1-3-carbethoxyamino-4-carbomethoxyamino-2-tetrahydrothiophenevaleric acid piperidide as a colorless oil.

EXAMPLE 10

0.320 g (.00077 mole) of all cis d,1-3-carbethoxyamino-4-carbomethoxyamino-2-tetrahydrothiophenevaleric acid piperidide was dissolved in 5 ml (0.005 mole) of 1 N sodium hydroxide. The reaction solution was refluxed 4.0 hrs. At this point, the solution was partitioned between 10 ml of water and 25 ml of methylene chloride. The basic aqueous phase was extracted three times with 20 ml portions of dichloromethane. The aqueous phase was acidified with 7 ml of 1 N hydrochloric acid. The solvent was removed to leave a white, crystalline residue, containing cis-d,1-3-amino-4-amino-tetrahydrothiophenevaleric acid and d,1-biotin. This residue was taken up in 15 ml of 10% by weight aqueous potassium carbonate solution, and gaseous phosgene was bubbled into the reaction mixture at 0°C. until acidic to congo red.

After two hours at 25°C., the reaction mixture was evaporated to dryness. The d,1-biotin residue was suspended in 70 ml of anhydrous methanol and treated with 1 drop of conc. sulfuric acid. The reaction was refluxed for one hour, cooled, and filtered. The filtrate was evaporated, and the residue was partitioned between 40 ml of dichloromethane and 25 ml of water. The aqueous phase was further extracted twice with 15 ml portions of dichloromethane. The organic phases were combined, dried over anhydrous sodium sulfate, and evaporated to afford 0.080 g (0.00031 mole, 40%) of crude d,1-biotin methyl ester. The product was chromatographed on one silica thick layer plate which was eluted with benzene: ethyl acetate: glacial acetic acid (55:35:10 parts by volume). Isolation of the band at $R_f$ = 0.4 gave (0.000015 mole, 20%) of pure d,1-biotin methyl ester; m.p. 131°–132°C.

EXAMPLE 11

0.455 g (0.001 mole) of 3-(N-carbethoxyacetamido)-4-carbomethoxyamino-2,5-dihydro-2-thiophenevaleric acid piperidide was dissolved in 200 ml of glacial acetic acid and subjected to 1800 psi hydrogen gas in a steel autoclave at 75°C. for 10 hrs., in the presence of 2.5 g 10% Pd/C catalyst. After cooling to room temperature (22°C.), the autoclave was vented, and the catalyst filtered and washed with 100 ml of glacial acetic acid. The solvent was removed under high vacuum to afford 0.400 g (0.0087 mole, 95%) of all cis-d,1-3-(N-carbethoxyacetamido)-4-carbomethoxyamino-2-tetrahydrothiophenevaleric acid piperidide as a colorless oil.

EXAMPLE 12

0.400 g (.00088 mole) of all cis d,1-3-(N-carbethoxyacetamido)-4-carbomethoxyamino-2-tetrahydrothiophenevaleric acid piperidide was added to a suspension of 10.0 g $Ba(OH)_2·8H_2O$ in 50 ml of water. The heterogeneous reaction mixture was heated at 140°C. for 24 hrs. in a sealed tube.

After cooling, the reaction mixture was treated with gaseous $CO_2$ until the pH was lowered to 5. After filtration, the filtrate was acidified to congo red with 1 N sulfuric acid and filtered once again. The filtrate was evaporated to dryness. The cis-d,1-3-amino-4-aminotetrahydrothiophenevaleric acid residue was dissolved in 15 ml of 10% by weight aqueous potassium carbonate solution. Gaseous phosgene was bubbled into the solution at 0°C. until acid to congo red. After 2.0 hrs. at 25°C., the reaction mixture was evaporated to dryness. The d,1-biotin residue was suspended in 25 ml of anhydrous methanol, and 1 drop of concentrated sulfuric acid was added.

After refluxing for 45 minutes, the reaction was cooled and filtered, and the filtrate was evaporated. The residue was partitioned between 40 ml of dichloromethane and 20 ml of water.

The aqueous phase was further extracted twice with 15 ml portions of dichloromethane. The organic phases were pooled, dried over anhydrous sodium sulfate, and evaporated to afford 0.100 g (0.000388 mole, 44%) of crude d,1-biotin methyl ester. The product was chromatographed on one silica thick layer plate. Elution was with benzene: ethyl acetate: glacial acetic acid (55:35:10 parts by volume). The band at $R_f$ = 0.4 was isolate to afford 0.031 g (0.000012 mole), 14%) of d,1-biotin methyl ester.

We claim:
1. A compound of the formula:

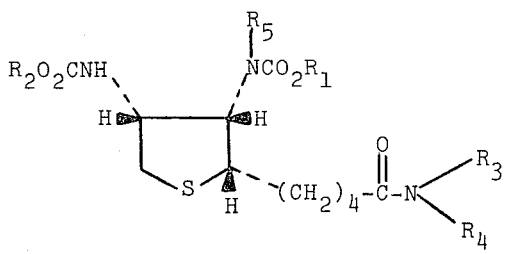

wherein $R_1$ is lower alkyl; $R_2$ is aliphatic hydrocarbyl; $R_3$ and $R_4$ may be taken together with the nitrogen atom to form a piperidide ring; $R_5$ is hydrogen or

and $R_6$ is lower alkyl.

2. The compound of claim 1 wherein said compound is all cis-d,1-3-carbethoxyamino-4-carbomethoxyamino-2-tetrahydrothiophenevaleric acid piperidide.

3. The compound of claim 1 wherein said compound is all cis-d,1-3-(N-carbethoxyacetamido)-4-carbomethoxyamino-2-tetrahydrothiophenevaleric acid piperidide.

4. A process for obtaining a compound of the formula:

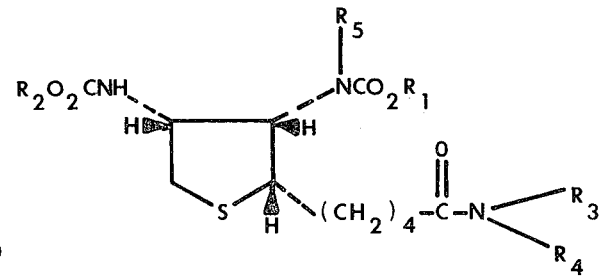

wherein $R_1$ is lower alkyl; $R_2$ is aliphatic hydrocarbyl; $R_3$ and $R_4$ may be taken together with the nitrogen atom to form a piperidide ring; $R_5$ is hydrogen or

and $R_6$ is lower alkyl;
comprising hydrogenating a compound of the formula:

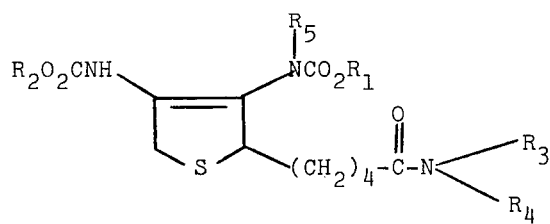

wherein $R_1$, $R_2$, $R_3$, $R_4$ and $R_5$ are as above in the presence of a noble metal catalyst and a carboxylic acid at a temperature of about 50°C to 110°C.

5. The process of claim 4 wherein said noble metal catalyst is palladium, platinum, ruthenium or rhodium.

6. The process of claim 5 wherein said catalyst is palladium.

7. The process of claim 4 wherein said process is carried out in glacial acetic acid.

* * * * *